United States Patent [19]
Kawaguchi

[11] Patent Number: 5,269,680
[45] Date of Patent: Dec. 14, 1993

[54] CERAMIC BRACKET WITH COATED BASE

[75] Inventor: Kozo Kawaguchi, Ohkuma, Japan

[73] Assignee: Tomy K.K., Tokyo, Japan

[21] Appl. No.: 850,884

[22] Filed: Mar. 13, 1992

[30] Foreign Application Priority Data

Mar. 4, 1992 [JP] Japan ................................ 4-081471

[51] Int. Cl.$^5$ ................................................ A61C 3/00
[52] U.S. Cl. ............................................ 433/9; 433/24
[58] Field of Search ....................... 433/8, 9, 24, 217.1

[56] References Cited

U.S. PATENT DOCUMENTS 4,826,430 5/1989 Chen et al. ................................ 433/9
4,948,366 8/1990 Horn et al. ................................ 433/9

OTHER PUBLICATIONS

Carroll G. Bennett, DDS, MS, Chiayi Shen, PhD., Joseph M. Waldron DDS, "The Effects of Debonding on the Enamel Surface," J.C.O., May 1984, pp. 330-334.

Brochure on Ceramic Debonding Units from Dentaurum, Inc., pp. 18-33.

Primary Examiner—Cary E. O'Connor
Attorney, Agent, or Firm—Kenyon & Kenyon

[57] ABSTRACT

A method of bonding ceramic brackets to teeth using silane coupling where the bond strength can be controlled by the application of a layer of organic paint. The method comprises the application of a silane coupling agent to the base surface of a bracket and the application of an organic paint to the entirety or a portion of the silane coupling agent such that when an organic adhesive is applied to the base surface of the bracket, the organic paint partially shields the silane coupling and thereby lowers the bond strength. The organic paint can be applied in different configurations to the silane coupling agent on the base surface of the bracket such that bond strength is decreased only over select areas of the base surface.

11 Claims, 2 Drawing Sheets

CERAMIC BRACKET WITH COATED BASE

BACKGROUND OF THE INVENTION a. Field of the Invention

This invention relates to controlling adhesive bond strength of orthodontic brackets. In particular, this invention pertains to the coating of the base of a ceramic orthodontic bracket that will be chemically bonded to teeth in order to control the adhesive bond strength between the bracket and a tooth. The invention is particularly applicable to bonding where silane coupling is used.

b. Description of the Prior Art

Ceramic brackets for adhesive bonding to teeth are a recent development in the field of orthodontics. Such materials are of high structural strength so as to provide a superior product that will last over the typical two to three years length of treatment. In addition, these materials have optical properties that render them translucent or transparent. This provides a cosmetic advantage of being inconspicuous in the mouth.

Methods of adhering ceramic brackets to teeth can be broken down into mechanical bonding and chemical bonding. Mechanical bonding includes: (1) products furnished with channels and holes in the adhesive surface, (2) products furnished with multiple projections on the adhesive surface, an (3) products with fine particles of ceramic or glass sprinkled over and adhered to the adhesive surface. Chemical bonding includes: (1) products with silane couplings painted on the adhesive surface, (2) products with the base surfaces covered with a silica glass that bonds chemically with the adhesive, and (3) products where the base elements are formed of plastic and this plastic bonds chemically with the dental adhesive.

Chemical bonding using silane couplings are very strongly adhered to tooth surfaces. This high adhesive bond strength prevents the bracket from peeling away from the tooth during a normal treatment period, however, it can also make bracket removal difficult.

A method for controlling the bond strength between the inorganic bracket and the organic adhesive using silane coupling is disclosed in U.S. Pat. No. 4,948,366. That approach is to apply a mixture of organofunctional silane coupling agents, one which is reactive, the other non-reactive with the organic resin of the adhesive. When the organic adhesive is applied, it reacts with the silane coupling agent in proportion to the amount of reactive organofunctional silane coupling agent present. According to the patent, by varying the proportions of reactive and non-reactive silane coupling components of the mixture, the bond strength can be varied. Another method proposed to debond ceramic brackets involves the application of heat to the bracket by means of a short time contact. The application of heat must however be controlled so that it is sufficient to soften the adhesive but not to cause damage to the tooth. While this technique and others have met with some degree of success, none provide an optimal solution to the present disadvantages of debonding.

During debonding, force is applied to the base or the wings of a bracket to overcome the bond strength of the adhesive. This applied force does not, however, create a constant stress across the entire bonded area. Debonding techniques create differential stresses across the tooth enamel, in the adhesive, and in the bracket. The type and location of the stress created varies depending upon the debonding method used. The adhesive-bracket interface can be broken, leaving adhesive on the tooth surface that must be removed with a rotary grinder. More serious problems arise when the adhesive-enamel interface is broken because the tooth enamel can be damaged.

OBJECTIVES AND SUMMARY OF THE INVENTION

In view of the shortcomings of the prior art, it is an object of the present invention to provide a method for controlling bond strength.

It is a further object of the present invention to provide for ceramic orthodontic brackets, particularly where silane coupling has been used, which can be safely and easily bonded and debonded from teeth.

It is a further object of the present invention to provide a method of site-specifically varying and controlling the bond strength across the interface between a substrate and an adhesive, particularly where silane coupling is being used, to facilitate treatment and removal where a given removal technique creates differential stresses across that interface.

It is a further object of the present invention to provide a method for adjusting the bond strength per unit area of individual brackets to be applied to a set of teeth such that different sized brackets bonded to different teeth in a patient may be affixed with nearly identical strengths.

Another object of the present invention is to provide a ceramic orthodontic bracket with a pigmented coating on the base surface such that matching of color between the teeth and the translucent or semitranslucent ceramic brackets can be achieved.

Briefly, the invention provides a method for controlling bond strength by coating the base of an orthodontic bracket comprising the steps of: coating a bracket base surface with a silane coupling agent; coating the entirety or a portion of the silane coupling agent with an organic paint; and reacting the silane coupling agent, totally or partially shielded by the organic paint, with an organic adhesive such that the bond strength obtained on the portions of the substrate surface where the silane coupling agent has been coated with the organic paint is less than the bond strength obtained on the portions of the substrate surface where the silane coupling agent has not been coated with the organic paint.

DETAILED DESCRIPTION OF THE INVENTION

Figure 1:
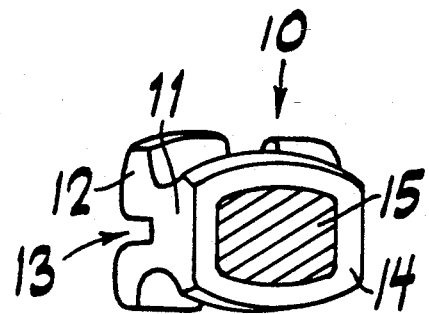
FIG. 1 shows the base surface of an orthodontic bracket that has been coated with a layer of organic paint for the purpose of shielding the bonding between the underlying substrate and the adhesive that will be applied.

FIG. 1 illustrates a typical orthodontic bracket 10 with a body 11, tie wings 12, archwire slot 13, and base surface 14. The base surface 14 should be curved so as to approximate the curvature of a tooth surface and thereby make a suitable fit onto the tooth surface after bonding. The bracket in FIG. 1 is only an example of an orthodontic bracket suitable for use in the present invention. Other designs that add to, omit or replace any of the illustrated components or any other orthodontic appliance with a base to be bonded to the tooth surface would be acceptable.

A preferred bracket would be made of ceramic, particularly a polycrystalline alumina ceramic with an average particle diameter of 10 to 30 $\gamma$ and light permeation of 70 to 80%. These brackets are high strength and have the cosmetically desirable optical property of preferably being translucent or transparent. Other ceramics, metals or plastics may also be used. Examples of other suitable materials include light permeable zirconia or monocrystalline ceramics, tempered glass, tempered plastic, stainless steel or titanium brackets.

Although alumina ceramics are desirable materials for orthodontic appliances because of their mechanical and optical properties, alumina does not bond well with most dental adhesives. Silica that has been silanated with a coupling agent exhibits stronger bonding with conventional dental adhesives. As a result, an alumina substrate may be coated with a layer of silica-containing material. In order to facilitate bonding with an organic adhesive, the silica-containing layer is coated with a silane coupling agent which changes the character of the silica-containing surface from an inorganic silica layer to an organic moiety of the silane coupling agent. Once the substrate has been silanated, applying an organic adhesive creates a very high strength bond. It has been discovered that the strength of the bond between the adhesive and the substrate may be reduced by utilization of a layer of organic paint applied between the substrate and the adhesive for the purpose of shielding the bonding and thereby reducing the strength of the bond.

Figure 2:
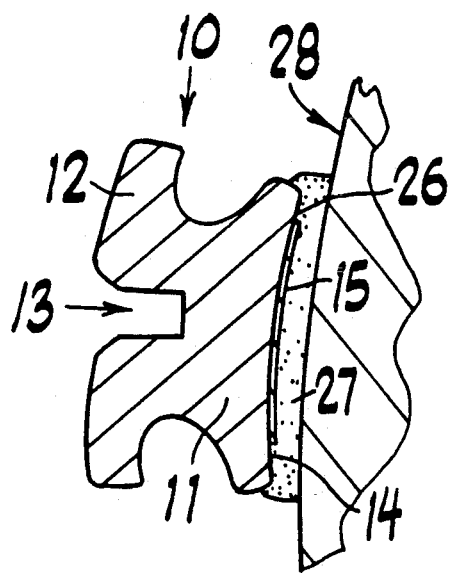
FIG. 2 shows a cross-sectional view of a typical bracket that has been bonded to a tooth in accordance with this invention.
Figure 3C:
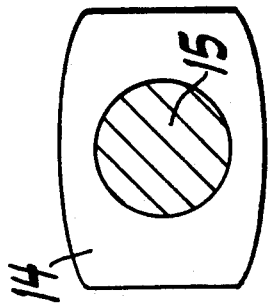
FIG. 3 shows different example configurations of paint applied to the surface of a bracket base to facilitate specific area shielding of the bonding between the underlying substrate and the adhesive that will be applied.
Figure 3B:
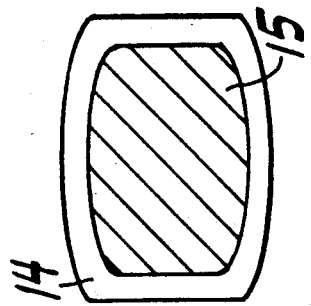
Figure 3D:
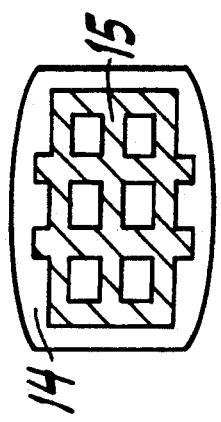
Figure 3A:
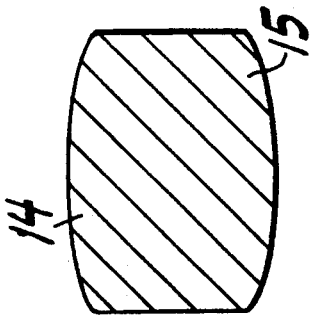

FIG. 2 shows a cross-sectional view of a bracket on a tooth that may be bonded in accordance with this invention. A bracket 10 with body 11, tie wings 12, archwire slot 13, and base surface 14 can be bonded to the tooth surface 28. Where the bracket is made from alumina, a silica containing layer may be first deposited on the base surface 14 if so desired. The application of a silane coupling agent creates a silane layer 26 on the base surface 14. A layer of organic paint 15 is then selectively applied to the surface of the silane layer 26. An adhesive layer 27 is then applied to bond the bracket 10 to the tooth surface 28.

Conventional dental adhesives contain organic materials. In the present invention, conventional acrylate or methacrylate dental adhesives are preferred. Many dental adhesives are commercially available which contain methacrylic resins. The adhesives are applied to the base surface of a bracket immediately before bonding to a patient's tooth and these adhesives are preferred because they create a strong bond that is stable in the oral environment. Additionally, these adhesives set quickly so as to minimize the time necessary for a patient to remain in the orthodontist's office. Preferred adhesives include bis-GMA type, PMMA type (polymethyl methacrylate type), and MMA type (methyl methacrylate type). Although these adhesives are preferred, other adhesives including light activated acrylic cements that will perform with the application of the organic paint may also be used.

The silane coupling agent is applied to the bottom surface of the bracket (which may optionally contain silica) in order to facilitate bonding of the bracket to the organic dental adhesive. A preferred silane coupling agent is gamma-methacryloxypropyltrimethoxy-silane. This silane coupling agent is particularly useful with acrylic and methacrylic resin dental adhesives. Other silane coupling agents from other groups may also be used depending on their reactivity with a particular dental adhesive.

The layer of organic paint is applied as illustrated for example in FIG. 1 in order to reduce the high bond strength created through the silane coupling mechanism. Removal of brackets from teeth becomes difficult if the bond strength is too high, as can be the case where silane coupling is being used. By coating the entirety or a portion of the silane layer with an organic paint, the bond strength can be reduced. The organic paint has a shielding effect on the silane coupling.

The layer of organic paint can be applied to the silane layer by any conventional coating technique. Examples include printing methods such as offset printing or silk printing, extruding viscous fluids with a dispenser, or painting with a brush. Any coating method that enables one to vary the area of the coating would be acceptable. Preferable paints are acrylic type, readily available and typically used with dental adhesives. Urethane, alkyd, and fluorine paints may also be used as long as they are not harmful to the human body. When used with translucent brackets, it is advantageous to mix an opaque paint or ink to the organic paint coating to impart a slight opacity. The opacity is sufficiently visible to allow verification that the bracket has been coated without effecting the translucency of the bracket.

The adhesive strength is controlled by varying the area of the organic paint coating. Although the shielding mechanism of the organic paint varies with the paint used, the strength of the bond is lowered by the application of the layer of paint. During debonding, there is (1) separation of the interface between the silane coupling agent and the organic paint, (2) separation of the organic paint itself, and (3) peeling from the interface between the organic paint and the adhesive.

Taking the adhesive strength between the base surface treated with a silane coupling agent and an acrylic type adhesive as being 100%, test results have shown the strength of surfaces completely coated with acrylic paint to be about 40%. For example, when the peeling strength of the silane coupling treated surface of an upper central tooth bracket is 30 kg, the strength of a bracket with a paint coating covering 60% of the base surface area is $0.4 \times 0.6 \times 30 = 7.2$ kg in the area of the coating and $0.4 \times 1.0 \times 30 = 12$ kg in the uncoated area. This creates a bracket bonded with a peeling strength of $7.2 + 12 = 19.2$ kg. Because the ideal strength is 15 to 20 kg at the start of treatment and 10 to 15 kg at the time of bracket removal after two to three years, the effectiveness of the present method of bond strength control is apparent.

A further advantage of the present invention relates to the ability to vary and control the bond strength of a bracket to suit the needs of a particular tooth in a particular location in the mouth. Brackets vary in size depending on the tooth location in the mouth. For example, because the teeth in the upper jaw are larger than the teeth in the lower jaw, the base surface of a bracket for an upper central incisor may be about two-fold larger than a base surface of a bracket for a lower central incisor. Consequently, without a method for controlling the bond strength, the adhesive strength per unit of area ends up weaker for the lower central incisors and stronger than necessary for the upper central incisors. In order to avoid problems such as these, for example, it is possible to realize nearly identical strengths by coating 70% of the silane surface for the upper central incisor brackets and by not applying a coating to the lower central incisor brackets.

Different removal techniques create different stresses throughout the bracket base/tooth surface bonding interface. It is desirable to achieve a high bond strength in the areas that will be subjected to greater removal forces and a weaker bond strength in areas that subjected to lesser forces. Paint can be applied to the base surface of the bracket in a number of patterns in order to achieve this performance goal of the present invention. FIG. 3 represents four example configurations of paint covering different areas on the base surface of the bracket. The entire surface may be painted as shown in 3(a). This creates a uniformly distributed decrease in bond strength across the entire base surface. In 3(b), the base surface with the exception of the edges are painted, and in 3(c), only the center of the base surface is painted. Both the configurations in 3(b) and 3(c) create a bracket that is bonded more weakly in the center and more strongly around the edges. In 3(d), the paint is applied in a lattice. This has the effect of more uniformly distributing the overall bond strength shielding across a larger area of the base surface while maintaining strongly bonded areas of unpainted area dispersed across the entire base surface area.

Preferred configurations of the paint on the base surface of a bracket are represented by 3(b) and 3(c). In both of these configurations, the silane coupling is not shielded around the edges of the bracket. A strong bond is thereby maintained around the outer perimeter of the base surface, while closer to the center, the bond strength is decreased by the shielding of the organic paint. It has been found particularly effective to apply an organic paint to approximately 60% of the base surface for brackets to be applied to central, cuspids and bicuspids, and 50% of the base surface for brackets to be applied to upper lateral and lower anterior teeth. It is also preferred to apply the organic paint in a thickness of 0.03 to 0.10 mm and most preferred in the range of 0.05 to 0.07 mm.

One reason for preferring the 3(b) and 3(c) configurations is to compensate for the effect on the enamel imparted during bracket removal. When a bracket is clasped in the distal and mesial directions for lifting out, the bracket base incurs the maximum stress at the portion almost directly beneath its center. Coating the central portion is therefor safer for the enamel than having a uniform adhesive strength over the entire surface of the bracket base.

Another reason for preferring this configuration is for moisture resistance. Moisture such as saliva is always forming in the mouth. The temperature effects of hot tea or cold ice cream are also felt. When there is no moisture resistance, molecules of water gradually intrude from the interface between the bracket base and the adhesive, lowering the adhesive strength. Before two years have passed, the bracket ends up peeling from the tooth surface. The interface between the adhesive and the ceramic with silane interposed gives high moisture resistance, and no extreme decrease in strength is found even after heating and cooling cycles.

In the foregoing specification, the present invention has been described with respect to specific embodiments. These serve as examples to illustrate the invention rather than limit its scope. Modifications may be made without departing from the broader teachings of the invention.

What is claimed is:

1. A method of controlling the bond strength between an inorganic orthodontic bracket and an organic adhesive comprising the steps of:
    coating a base surface of the bracket with a silane coupling agent;
    coating at least a portion of the silane coupling agent with an organic paint; and
    reacting the silane coupling agent, selectively shielded by the organic paint, with an organic adhesive such that the bond strength obtained on the portions of the base surface where the silane coupling agent has been coated with the organic paint is less than the bond strength obtained on the portions of the base surface where the silane coupling agent has not been coated with the organic paint.

2. The method according to claim 1 wherein the organic paint is applied to the silane coupling agent on the base surface in a lattice pattern.

3. The method according to claim 1 wherein the organic paint is applied to approximately 50–60% of the silane coupling agent on the base surface in the central area of the base surface and not around the edge of the base surface.

4. A method for bonding an orthodontic bracket to a tooth comprising the steps of:
    applying a silane coupling agent to a base surface of the bracket;
    applying a layer of organic paint on at least to a portion of the base surface on top of the silane coupling agent; and
    bonding the bracket to a tooth by applying an organic adhesive to the treated base surface such that the bond strength obtained on the portions of the base surface where the silane coupling agent has been coated with the organic paint is less than the bond strength obtained on the portions of the base surface where the silane coupling agent has not been coated with the organic paint.

5. The method according to claim 4 wherein the organic paint is applied to the silane coupling agent on the base surface in a lattice configuration.

6. The method according to claim 4 wherein the organic paint is applied in a thickness in the range of 0.03 to 0.10 mm to the silane coupling agent in the central area of base surface and not to the silane coupling agent around the edges of the base surface.

7. A method for bonding a ceramic orthodontic bracket to a tooth comprising the steps of:
    applying a silica-containing layer to a base surface of the bracket;
    applying a silane coupling agent to the base surface on top of the silica-containing layer;
    applying a layer of organic paint on at least a portion of the base surface on top of the silane coupling agent; and
    bonding the bracket to a tooth by applying an organic adhesive to the base of the bracket such that the bond strength obtained on the portions of the base surface where the silane coupling agent has been coated with the organic paint is less than the bond strength obtained on the portions of the base surface where the silane coupling agent has not been coated with the organic paint.

8. The method according to claim 7 wherein the organic paint is applied to the silane coupling agent on the base surface in a lattice configuration.

9. The method according to claim 7 wherein the organic paint is applied to approximately 50-60% of the silane coupling agent in the central area of base surface and not to the silane coupling agent around the edges of the base surface.

10. A ceramic orthodontic bracket comprising:
a ceramic body with a base surface;
a silica-containing layer on the base surface;
a silane coupling agent layer on the silica-containing layer, the silane coupling agent being reactive with an organic dental adhesive; and
an organic paint layer on the silane coupling agent layer that selectively shields the adhesive bonding potential of the silane coupling agent layer.

11. A set of ceramic orthodontic brackets comprising:
brackets for the teeth of the upper jaw;
brackets for the teeth of the lower jaw; and wherein each bracket has a base surface that has been treated by coating in succession with a silica-containing layer, a silane coupling agent layer, and an organic paint deposited selectively layer over the base surface area in accordance with the amount of tooth surface to be covered, such that when an organic adhesive is applied to the treated base surface, the bond strength obtained renders each bracket subject to substantially the same removal force.

* * * * *

UNITED STATES PATENT AND TRADEMARK OFFICE
CERTIFICATE OF CORRECTION

PATENT NO. : 5,269,680
DATED : December 14, 1993
INVENTOR(S) : Kozo KAWAGUCHI

It is certified that error appears in the above-indentified patent and that said Letters Patent is hereby corrected as shown below:

Column 1, line 19, change "years length" to --years' length--.

Column 1, line 28, change "an (3)" to --and (3)--.

Column 1, line 40, change "period, how-" to --period; how---.

Column 1, line 56, after "must" insert a comma.

Column 1, line 57, after "however" insert a comma.

Column 2, line 27, change "different sized brackets" to --different-sized brackets--.

Column 5, line 14, between "that" and "sub-" insert --will be--.

Column 5, line 41, do not make "60%" boldface.

Column 5, line 54, change "therefor" to --therefore--.

Column 6, line 35, change "at least to a por-" to --at least a por-"

UNITED STATES PATENT AND TRADEMARK OFFICE
CERTIFICATE OF CORRECTION

PATENT NO. : 5,269,680

DATED : December 14, 1993

INVENTOR(S) : Kozo KAWAGUCHI

It is certified that error appears in the above-indentified patent and that said Letters Patent is hereby corrected as shown below:

Column 6, line 52, between "of" and "base" insert --the--.

Column 7, line 8, between "of" and "base" insert --the--.

Signed and Sealed this

Twelfth Day of July, 1994

Attest:

BRUCE LEHMAN

Attesting Officer

Commissioner of Patents and Trademarks